(12) United States Patent
Hao et al.

(10) Patent No.: US 9,262,991 B2
(45) Date of Patent: Feb. 16, 2016

(54) DISPLAYING VISUAL ANALYTICS OF ENTITY DATA

(71) Applicant: Hewlett-Packard Development Company, L.P., Houston, TX (US)

(72) Inventors: Ming C. Hao, Palo Alto, CA (US); Michael Hund, Hauptstrasse (DE); Wei-Nchih Lee, Palo Alto, CA (US); Halldor Janetzko, Haupstrasse (DE); Nelson L. Chang, San Jose, CA (US); Daniel Keim, Haupstrasse (DE); Sebastian Mittelstaedt, Haupstrasse (DE)

(73) Assignee: Hewlett Packard Enterprise Development LP, Houston, TX (US)

(*) Notice: Subject to any disclaimer, the term of this patent is extended or adjusted under 35 U.S.C. 154(b) by 111 days.

(21) Appl. No.: 14/188,099

(22) Filed: Feb. 24, 2014

(65) Prior Publication Data

US 2015/0243247 A1    Aug. 27, 2015

(51) Int. Cl.
| | |
|---|---|
| G06T 11/00 | (2006.01) |
| G06T 11/60 | (2006.01) |
| G06T 11/20 | (2006.01) |
| G06T 5/00 | (2006.01) |
| G06T 3/40 | (2006.01) |
| G09G 5/02 | (2006.01) |
| G09G 5/377 | (2006.01) |

(52) U.S. Cl.
CPC .. G09G 5/02 (2013.01); G06T 3/40 (2013.01); G06T 5/002 (2013.01); G06T 11/20 (2013.01); G09G 5/377 (2013.01)

(58) Field of Classification Search
CPC combination set(s) only.
See application file for complete search history.

(56) References Cited

U.S. PATENT DOCUMENTS

| | | | |
|---|---|---|---|
| 8,015,183 B2 | 9/2011 | Frank | |
| 8,564,596 B2 | 10/2013 | Carrino et al. | |
| 2005/0027705 A1 | 2/2005 | Sadri et al. | |
| 2007/0014488 A1* | 1/2007 | Chen et al. | 382/294 |
| 2008/0104531 A1 | 5/2008 | Stambaugh | |
| 2011/0125397 A1* | 5/2011 | Lee | 701/201 |

(Continued)

FOREIGN PATENT DOCUMENTS

WO    WO-2012152982 A1    11/2012

OTHER PUBLICATIONS

"HealthMap", Google, Download Date: Feb. 24, 2014. <http://www.healthmap.org/about>.

(Continued)

*Primary Examiner* — Wesner Sajous
(74) *Attorney, Agent, or Firm* — Mannava & Kang

(57) ABSTRACT

According to an example, in a method for displaying visual analytics of entity data, geographic locations of entities may be plotted as first pixel cells on a first region and as second pixel cells on a second region of a geographic map. A determination may be made that the first pixel cells have a higher degree of overlap with each other in the first region compared to the second pixel cells in the second region. The geographic map may be distorted to enlarge the first region and the first pixel cells may be arranged in the first region in a manner that prevents the first pixel cells from overlapping each other. A color value for each of the pixel cells may be determined from a multi-paired color map that represents two variables corresponding to the entities by color and the pixel cells may be caused to be displayed on the distorted geographic map according to the determined respective color values.

15 Claims, 9 Drawing Sheets

(56) References Cited

U.S. PATENT DOCUMENTS

2011/0280453 A1* 11/2011 Chen et al. .................... 382/113
2013/0073336 A1 3/2013 Heath

OTHER PUBLICATIONS

"MapPoint", Microsoft, Download Date: Feb. 24, 2014. <http://www.microsoft.com/mappoint/en-us/home.aspx>.

"Understanding of the Efficiency and Effectiveness of the Health Care System", The Dartmouth Atlas of Health Care, Download Date: Feb. 24, 2014. <http://www.dartmouthatlas.org/>.

Krstajić, Miloš, et al., "Applied Visual Exploration on Real-Time News Feeds Using Polarity and Geo-Spatial Analysis", Proceedings of the 6th International Conference on Web Information Systems and Technology; Apr. 7-10, 2010, pp. 263-268.

* cited by examiner

DISPLAYING VISUAL ANALYTICS OF ENTITY DATA

BACKGROUND

Geographic maps are typically employed to display the locations of various objects within a particular area. Along with their respective geographic locations, additional information, such as a particular attribute of the various objects, is often provided on the geographic maps. Conventional geographic maps therefore provide an overview of the objects and a particular attribute of the objects.

BRIEF DESCRIPTION OF THE DRAWINGS

Features of the present disclosure are illustrated by way of example and not limited in the following figure(s), in which like numerals indicate like elements, in which.

DETAILED DESCRIPTION

Figure 1:
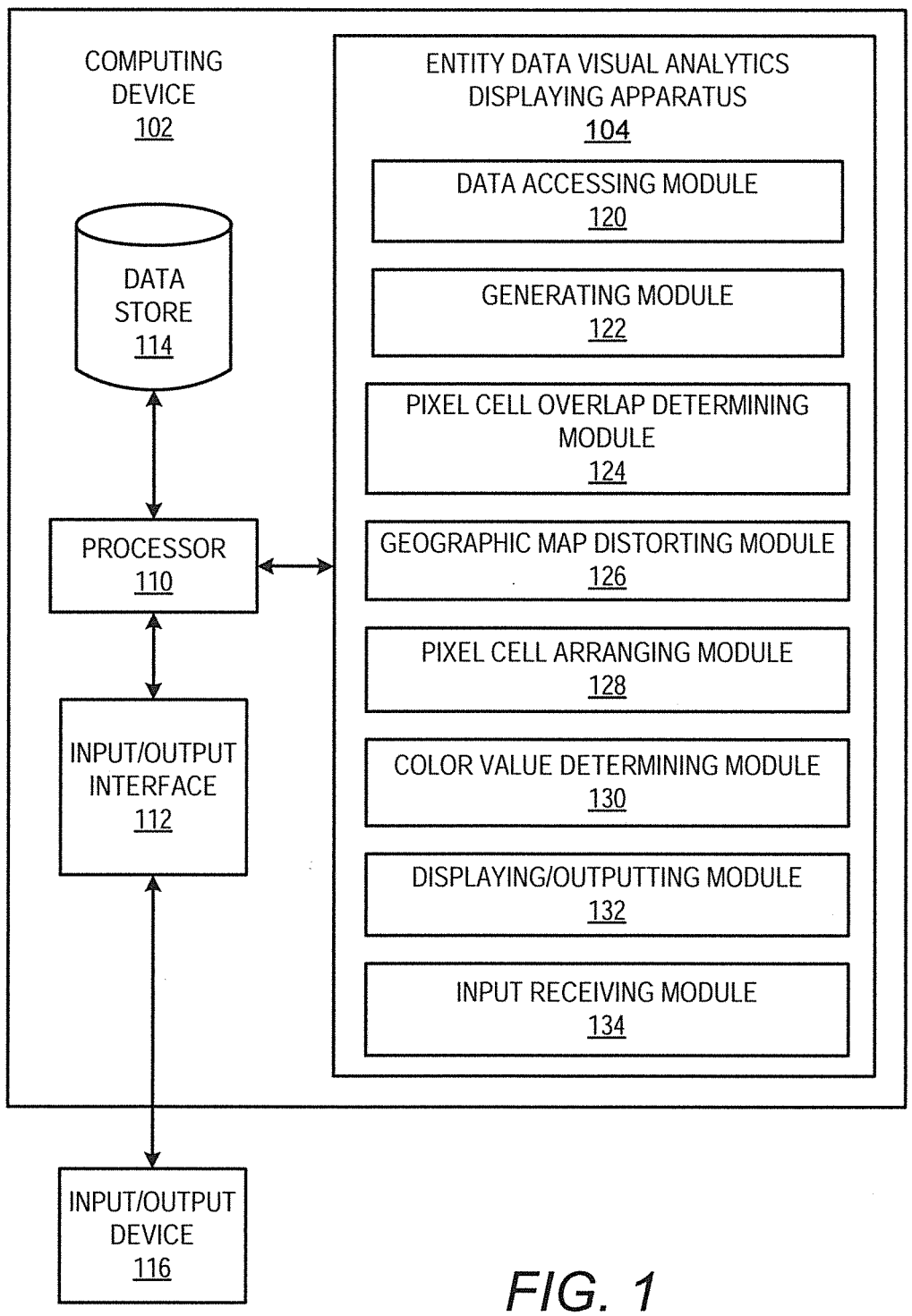
FIG. 1 is a simplified diagram of a computing device, which may implement various aspects of the methods disclosed herein, according to an example of the present disclosure.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Disclosed herein are methods for displaying visual analytics of entity data and apparatuses for implementing the methods. In the methods, geographic locations of a plurality of entities may be plotted as first pixel cells on a first region and as second pixel cells on a second region of a geographic map. In addition, a determination may be made that the first pixel cells have a higher degree of overlap with each other in the first region compared to the second pixel cells in the second region. The geographic map may be distorted to enlarge the first region and the first pixel cells may be arranged in the first region in a manner that prevents the first pixel cells from overlapping each other. Moreover, a color value for each of the first pixel cells and the second pixel cells may be determined from a multi-paired color map that represents two variables corresponding to the plurality of entities by color and the first pixel cells and the second pixel cells may be caused to be displayed on the distorted geographic map according to the determined respective color values.

Through implementation of the methods and apparatuses disclosed herein, visual analytics of high density spatial data may be visually provided as pixel cells on a map in a manner that may enable users to interactively and easily identify an entity or entities having desired attributes. In one regard, the visualization of the high density spatial data may enable pattern recognition and anomaly detection on a relatively large scale. In another regard, the interaction methods provided through implementation of the methods and apparatuses disclosed herein generally provide users with the ability to drill down into the data pertaining to the entities to thus make more informed decisions.

By way of particular example, the entities are hospitals, some of which may be located with respect to each other in a relatively dense manner, as may occur in relatively densely populated regions, while others may be located with respect to each other in a relatively less dense manner, as may occur in more rural regions. In this example, the variables corresponding to the hospitals may be hospital charges and services quality. As discussed in greater detail herein below, the methods and apparatuses disclosed herein may provide an interactive visualization of the analytics of the hospital data displayed as pixel cells to enable a user to compare the hospitals based upon their locations as well as data corresponding to the hospitals. This example is described in detail below with respect to FIGS. 7A-7E.

With reference first to FIG. 1, there is shown a simplified block diagram 100 of a computing device 102, which may implement various aspects of the methods disclosed herein, according to an example. It should be understood that the computing device 102 depicted in FIG. 1 may include additional elements and that some of the elements depicted therein may be removed and/or modified without departing from a scope of the computing device 102.

As shown in FIG. 1, the computing device 102 may include an entity data visual analytics displaying apparatus 104, a processor 110, an input/output interface 112, and a data store 114. The entity data visual analytics displaying apparatus 104 is also depicted as including a data accessing module 120, a generating module 122, a pixel cell overlap determining module 124, a geographic map distorting module 126, a pixel cell arranging module 128, a color value determining module 130, a displaying/output module 132, and an input receiving module 134.

The processor 110, which may be a microprocessor, a micro-controller, an application specific integrated circuit (ASIC), or the like, is to perform various processing functions in the computing device 102. The processing functions may include invoking or implementing the entity data visual analytics displaying apparatus 104 and particularly, the modules 120-134 of the entity data visual analytics displaying apparatus 104, as discussed in greater detail herein below. According to an example, the entity data visual analytics displaying apparatus 104 is a hardware device on which is stored various sets of machine readable instructions. The entity data visual analytics displaying apparatus 104 may be, for instance, a volatile or non-volatile memory, such as dynamic random access memory (DRAM), electrically erasable programmable read-only memory (EEPROM), magnetoresistive random access memory (MRAM), memristor, flash memory, floppy disk, a compact disc read only memory (CD-ROM), a digital video disc read only memory (DVD-ROM), or other optical or magnetic media, and the like, on which software may be stored. In this example, the modules 120-134 may be software modules, e.g., sets of machine readable instructions, stored in entity data visual analytics displaying apparatus 104.

In another example, the entity data visual analytics displaying apparatus 104 may be a hardware component, such as a chip, and the modules 120-134 may be hardware modules on the hardware component. In a further example, the modules 120-134 may include a combination of software and hardware modules.

The processor 110 may store data in the data store 114 and may use the data in implementing the modules 120-134. For instance, entity data that is to be used in generating the display of the visual analytics corresponding to the entity data may be stored in the data store 114. In addition, generated versions of maps containing pixel cells corresponding to the entity data may also be stored in the data store 114. In any regard, the data store 114 may be volatile and/or non-volatile memory, such as DRAM, EEPROM, MRAM, phase change RAM (PCRAM), memristor, flash memory, and the like. In addition, or alternatively, the data store 114 may be a device that may read from and write to a removable media, such as, a floppy disk, a CD-ROM, a DVD-ROM, or other optical or magnetic media.

The input/output interface 112 may include hardware and/or software to enable the processor 110 to communicate with other devices. For instance, the input/output interface 112 may enable the processor 110 to access a network, such as an internal network, the Internet, etc. The input/output interface 112 may include a network interface card and may also include hardware and/or software to enable the processor 110 to communicate with various input and/or output devices 116, such as a keyboard, a mouse, a display, another computing device, etc., through which a user may input instructions into the computing device 102 and may view outputs from the computing device 102. According to an example, the output device 116 is located outside of a network in which the computing device 102 is located. In this example, for instance, the computing device 102 may be located in a data center and the output device 116 may be located at an external location such that the computing device 102 may communicate data to the output device 116 over an external network, such as the Internet. In one regard, the output device 116, which may be another computing device, may access the computing device 102 over a cloud computing environment.

Figure 2:
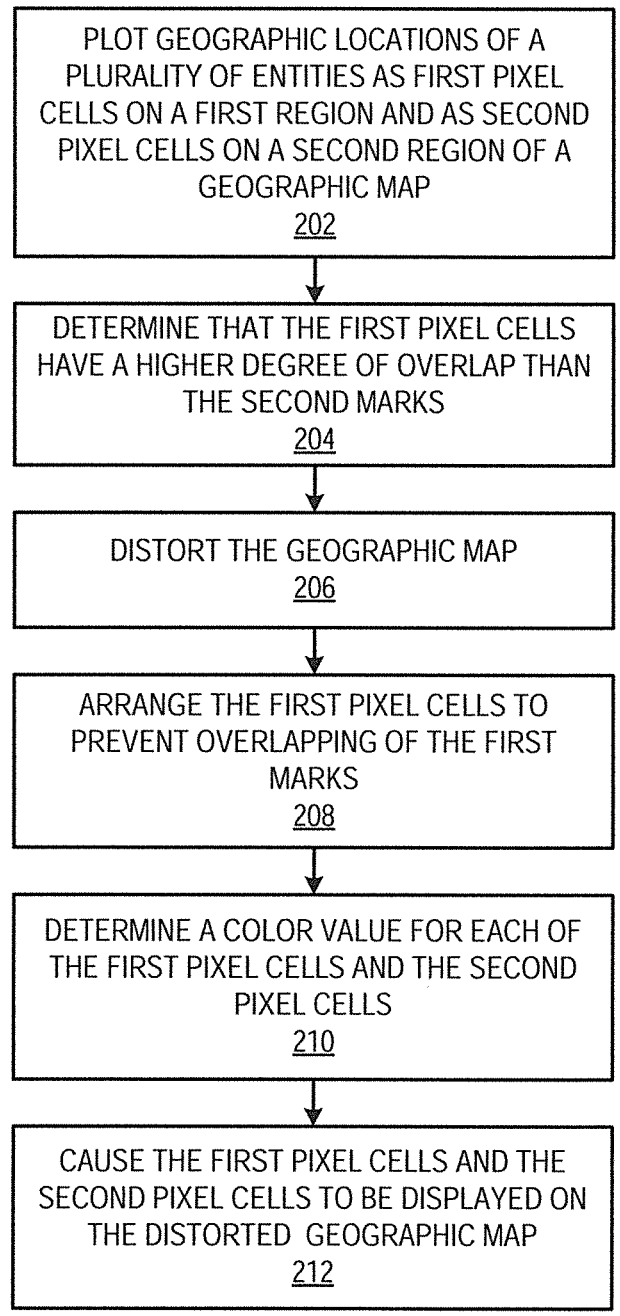
FIGS. 2 and 3, respectively, are flow diagrams of methods for displaying visual analytics of entity data, according to two examples of the present disclosure.
Figure 3:
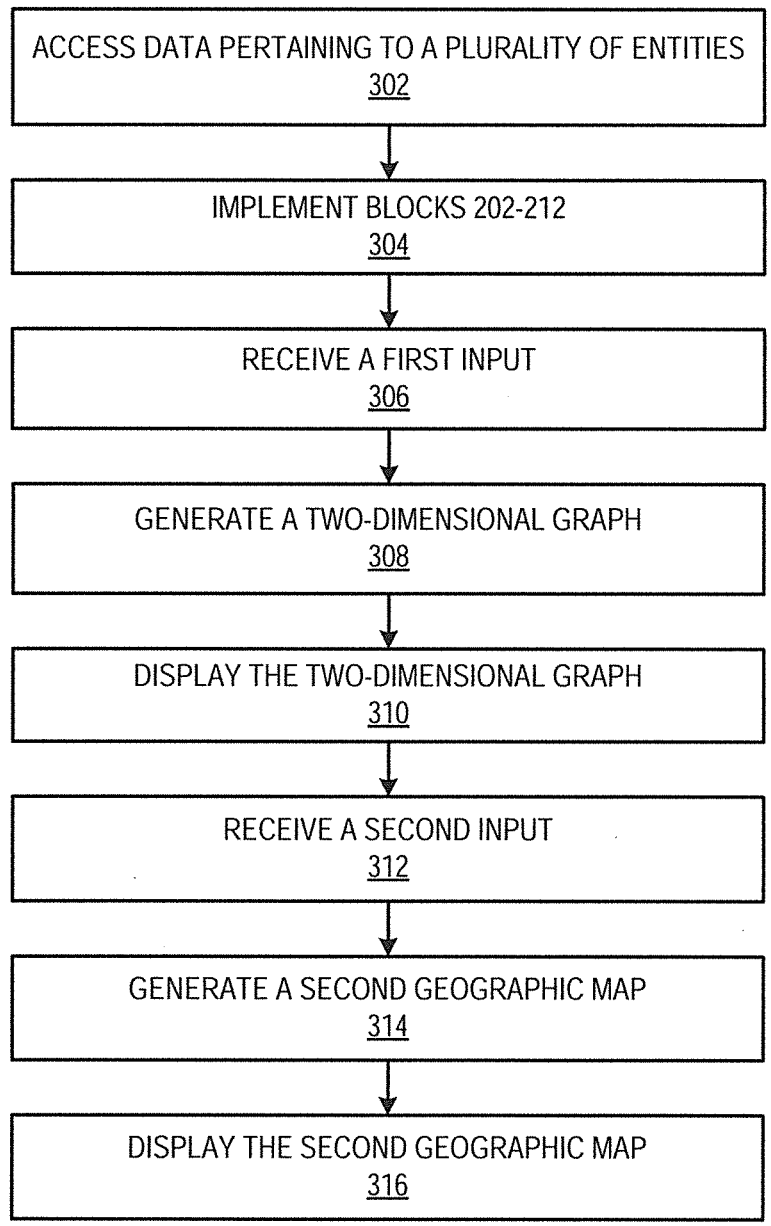

Various manners in which the processor 110 in general, and the modules 120-134 in particular, may be implemented are discussed in greater detail with respect to the methods 200 and 300 respectively depicted in FIGS. 2 and 3. Particularly, FIGS. 2 and 3, respectively, depict flow diagrams of methods 200 and 300 for displaying visual analytics of entity data, according to two examples. It should be apparent to those of ordinary skill in the art that the methods 200 and 300 may represent generalized illustrations and that other operations may be added or existing operations may be removed, modified, or rearranged without departing from the scopes of the methods 200 and 300. Generally speaking, the processor 110 depicted in FIG. 1 may implement the each of methods 200 and 300 through implementation of at least some of the modules 120-134.

The descriptions of the methods 200 and 300 are made with reference to the diagrams illustrated in FIGS. 4A-4C, 5, and 6A-6C. It should be clearly understood that the diagrams depicted in FIGS. 4A-4C, 5, and 6A-6C are for illustrative purposes only and should thus not be construed as limiting the scope of the present disclosure in any respect.

With reference first to FIG. 2, at block 202, geographic locations of a plurality of entities may be plotted as first pixel cells 410 on a first region 402 and as second pixel cells 412 on a second region 404 of a geographic map 400. Particularly, for instance, the processor 110 may implement the generating module 122 to plot the geographic locations of the entities as the first pixel cells 410 in the first region 402 of the geographic map 400. The processor 110 may also implement the generating module 122 to plot the geographic locations of the entities as the second pixel cells 412 in the second region 404 of the geographic map 400. Additionally, third pixel cells 414 may be plotted in the third region 406 and fourth pixel cells 416 may be plotted in the fourth region in similar manners.

By way of particular example, the geographic map 400 may be a geographic map of a particular area, such as the United States, a particular State or country, a county, a city, a neighborhood, a building, a field, etc. In addition, the regions 402-408 may be respective sections of the area, such as, individual states, individual counties, individual rooms, a regular grid, etc. The entities may be respective objects, buildings, land marks, etc., or collections of data, that are to be displayed on the geographic map 400. By way of particular example, the entities are hospitals, health care centers, revenue data, energy consumption data, etc.

Figure 4A:
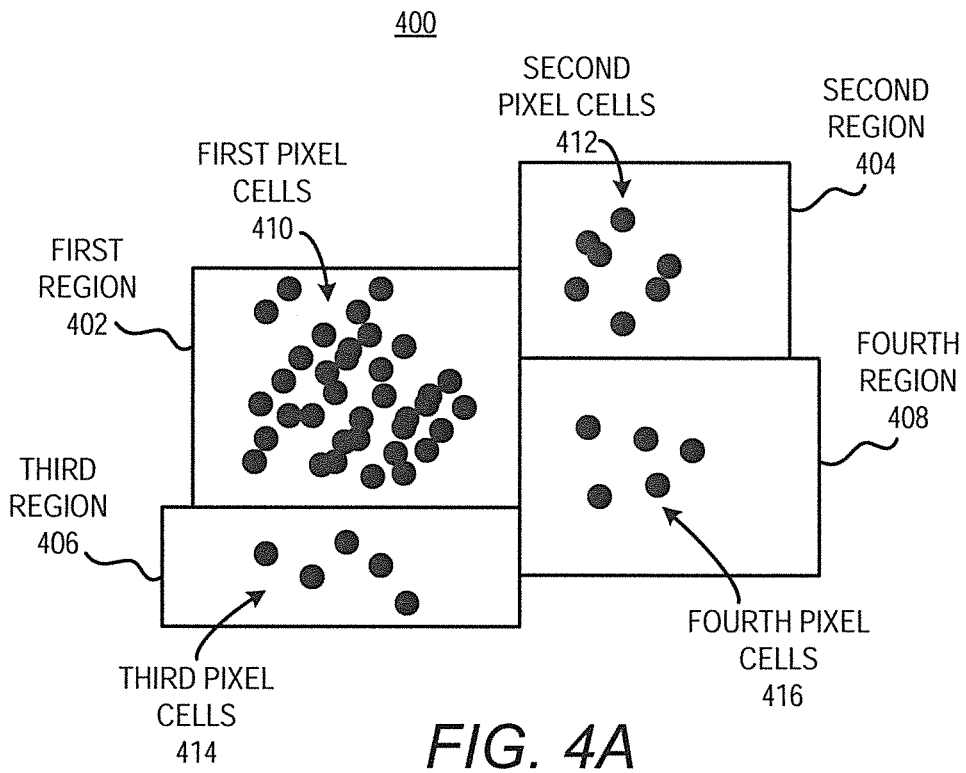
FIGS. 4A-4C, respectively, depict a geographic map at various stages of implementation of the method depicted in FIG. 2, according to an example of the present disclosure.

Although the pixel cells 410-416 are each depicted as circular dots in FIG. 4A, it should be understood that the pixel cells 410-416 may have any shape, such as squares, triangles, asterisks, textual characters, numbers, etc., without departing from a scope of the present disclosure. In addition, although the pixel cells 410-416 are depicted as having the same shapes, it should also be understood that some of the pixel cells 410-416 may have different shapes with respect to each other without departing from a scope of the present disclosure. For instance, the different shaped pixel cells may denote that their associated entities have different properties or attributes with respect to each other.

As discussed in greater detail below, the pixel cells 410-416 may also have any of a plurality of colors, in which the colors of the pixel cells 410-416 denote visual analytics of attributes, e.g., values, corresponding to the entities to which the pixel cells 410-416 respectively correspond.

At block 204, a determination may be made that the first pixel cells 410 have a higher degree of overlap with each other in the first region 402 as compared to the degree of overlap of the second pixel cells 412 in the second region 404. Particularly, the processor 110 may implement the pixel cell overlap determining module 124 to make this determination from the plotting of the pixel cells in the first and second regions 410, 412 of the geographic map 400. That is, the processor 110 may determine that a relatively larger number of first pixel cells 410 overlap each other than the number of second pixel cells 412 that overlap each other, if any. The first pixel cells 410 may have a higher degree of overlap with respect to other ones of the pixel cells 410, for instance, because the entities to which the first pixel cells 410 correspond may be in relatively close geographic proximities to each other.

At block 206, the geographic map may be distorted to enlarge the first region 402 containing the overlapping first pixel cells 410. Particularly, the processor 110 may implement the geographic map distorting module 126 to distort the first region 402 such that the first region 402 is enlarged, while keeping the other regions 404-408 unchanged. In addition, or alternatively, the processor 110 may implement the geographic map distorting module 126 to also distort the second region 404, for instance, to reduce the size of the second region 404. Thus, for instance, the processor 110 may distort some of the regions 402, 404 by enlarging or reducing those regions.

Figure 4B:
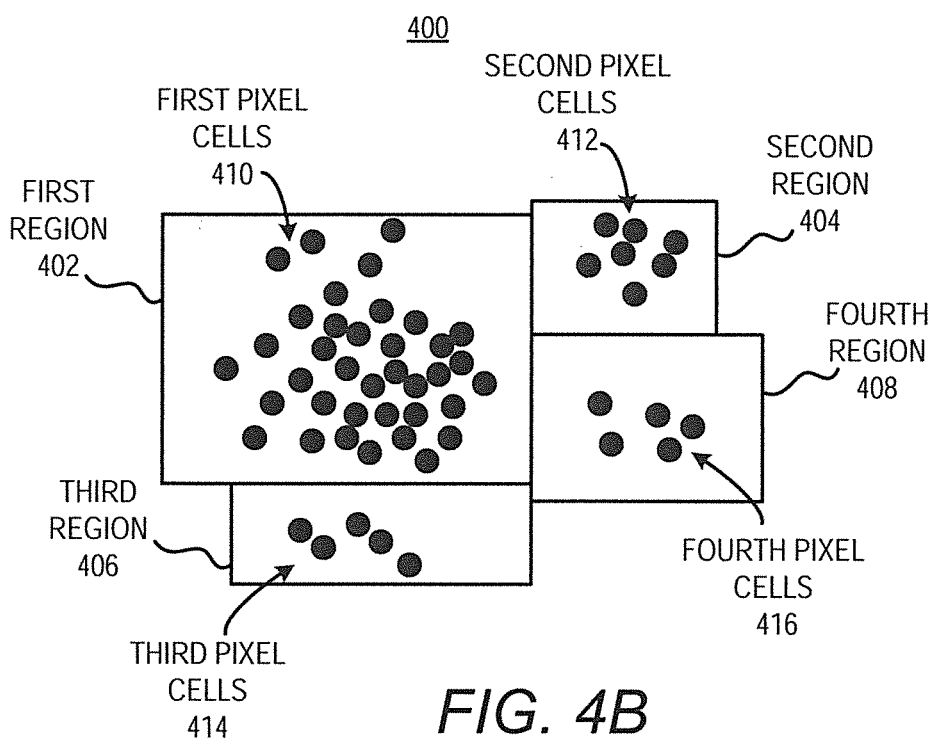

An example of the map 400 in which the first region 402 has been enlarged and second to fourth regions 404-408 have been reduced is show in FIG. 4B. As shown in FIG. 4A, the first pixel cells 410 in the first region 402 are arranged at a relatively higher density level as compared with the second pixel cells 412 in the second region 404. By enlarging the first region 402, the first pixel cells 410 are able to be arranged in over a larger space, while still enabling visualization of the entity locations with respect to each other.

According to an example, the processor 110 may implement a distortion technique that attempts to equalize the densities of the pixel cells in the respective regions 402-408 of the map 400. Thus, for instance, high density areas, e.g., the first region 402, may be enlarged, and low density areas, e.g., the second to fourth regions 404-408 may be reduced. The distortion technique may also include receipt of user input to further distort or to reduce the distortion of the regions 402-408. Thus, for instance, a user may iteratively manipulate the distortion of the regions 402-408 through a trial and error process to achieve a desired visualization of the entities on the map 400.

At block 208, the first pixel cells 410 in the first region 402 may be arranged in a manner that prevents the first pixel cells 410 from overlapping each other. For instance, the processor 110 may implement the pixel cell arranging module 128 to arrange the first pixel cells 410 in the first region 402 in a manner that prevents the first pixel cells 410 from overlapping each other. According to an example, the pixel cell arranging module 128 may include a pixel placement operation. That is, the pixel cell arranging module 128 may cause the processor 110 to iterate through all of the pixel cells in an ordered manner and check whether the original position, e.g., pixel position, of a pixel cell is already occupied by another pixel cell. If the original position of the pixel cell is not occupied by another pixel cell, the pixel cell may be placed at the original position. However, if the original position is occupied by another pixel cell, a closest free position, e.g., pixel position, may be determined and the pixel cell may be placed at the closest free position.

In instances in which multiple locations at which the pixel cell may be placed are the same distance away from the original position, the final position of the pixel cell may be determined to be a position that substantially optimizes the pixel cell placement based upon color. Thus, for instance, the final position of the pixel cell may be determined to be the location of the multiple locations that is the furthest away from a similarly colored pixel cell.

At block 210, a color value for each of the first pixel cells 410 and the second pixel cells 412 may be determined from a multi-paired color map that represents two variables corresponding to the plurality of entities by color. For instance, the processor 110 may implement the color value determining module 130 to determine the color value for each of the pixel cells 410-416 from a multi-paired color map. The multi-paired color map may represent multiple paired, two variables by color. For instance, an x-axis of the color map may represent a first variable and the y-axis of the color map may represent a second variable. In addition, the color map may be created by a bi-linear interpolation.

According to an example, the color map may be created using the hue, saturation, intensity (HSI) color space. For instance, the HSI color space may be used to create a coordinate system in which the origin of the coordinate system is mapped to the mean value of both variables (e.g., attributes) of the entities and the four corners of the coordinate system are mapped to a combination of min/max values of both variables (e.g., attributes) of the entities.

Figure 5:
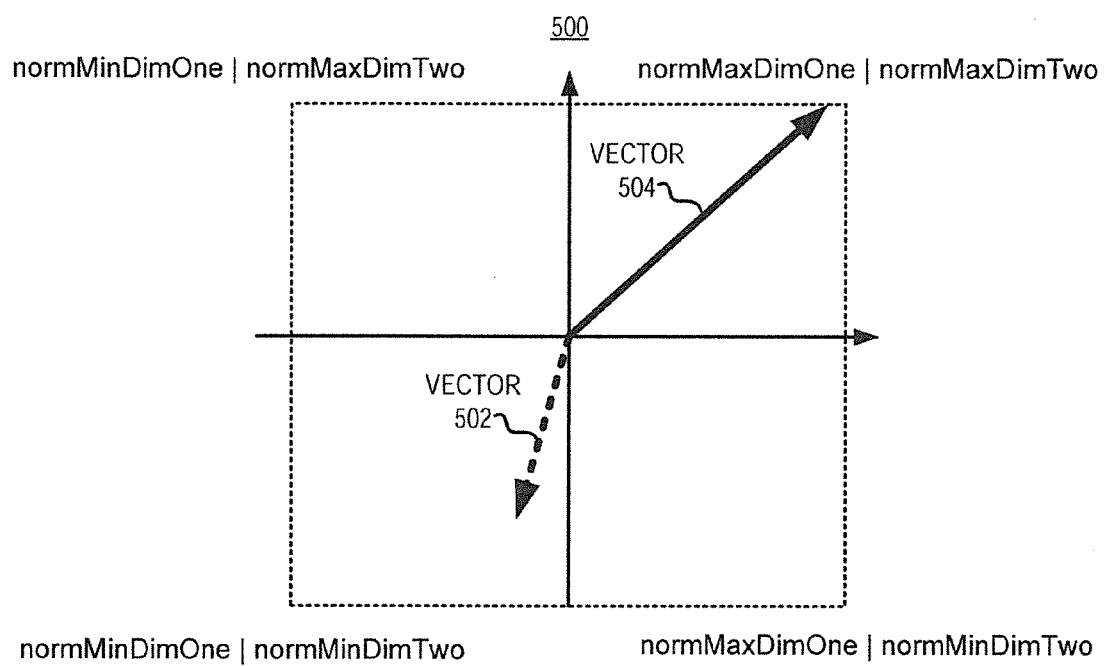
FIG. 5 depicts a color map that may be used to determine the color values of the pixel cells depicted in FIGS. 4A-4C, according to an example.

An example of a manner in which the final color of a pixel cell in the HSI color space is described with respect to FIG. 5, which depicts a color map 500, according to an example. Initially, the schema presented in FIG. 5 may be calculated through implementation of the following first operation:

```
INPUT: all values of attribute 1, all values of attribute 2,
  normalization method
OUTPUT: determine the values of the corners of the color map
// ==========================================================
// first dimension
if(normalization == LINEAR){
   normMinDimOne = min(attribute1);
   normMaxDimOne = max(attribute1);
}else if(normalization == SQRT){
   normMinDimOne = Math.sqrt(min(attribute1));
   normMaxDimOne = Math.sqrt(max(attribute1));
}else if(normalization == LOGARITHMIC){
   normMinDimOne = Math.log(min(attribute1));
   normMaxDimOne = Math.log(max(attribute1));
}
   normMeanDimOne = (normMinDimOne + normMaxDimOne) / 2;
// ==========================================================
// second dimension
if(normalization == LINEAR){
   normMinDimTwo = min(attribute2);
   normMaxDimTwo = max(attribute2);
}else if(normalization == SQRT){
   normMinDimTwo = Math.sqrt(min(attribute2));
   normMaxDimTwo = Math.sqrt(max(attribute2));
}else if(normalization == LOGARITHMIC){
   normMinDimTwo = Math.log(min(attribute2));
   normMaxDimTwo = Math.log(max(attribute2));
}
   normMeanDimTwo = (normMinDimTwo + normMaxDimTwo) / 2;
```

As may be noted in the first operation discussed above, the values of the corners of the color map 500 may be determined through application of one of a linear operation, a square root operation, and a logarithmic operation.

The color value for a given combination of two attributes (dimOne, dimTwo) may be obtained through implementation of the following techniques. Initially, the combination of both attributes may be transferred to the schema presented in FIG. 5 according to a second operation, which may calculate the normalized position in the coordinate system in the range [−1,+1] for each attribute. The result of the second operation may be a vector with a length between 0 and sqrt(2). The dashed vector 502 depicted in FIG. 5 is an example of the resulting vector. The second operation may include the following:

```
Input: value of the first attribute (dimOne), value of the second
  attribute (dimTwo)
Output:the normalized position in the range [−1,+1][−1,+1].
// normalize the input values (linear, sqrt or log)
if(normalization == SQRT){
   dimOne = Math.sqrt(dimOne);
   dimTwo = Math.sqrt(dimTwo);
}else if(normalization == LOGARITHMIC){
   dimOne = Math.log(dimOne);
   dimTwo = Math.log(dimTwo);
```

-continued

```
}
// first attribute
if(dimOne < normMeanDimOne){
    normalizedPosition[0] = (-1) * (1-normalize(dimOne,
    normMinDimOne, normMeanDimOne);
}else{
    normalizedPosition[0]    =    normalize(dimOne,
    normMeanDimOne, normMaxDimOne);
}
// second attribute
if(dimTwo < normMeanDimTwo){
    normalizedPosition[1] = (-1) * (1 -
    (normalize(dimTwo,normMinDimTwo,normMeanDimTwo);
}else{
    normalizedPosition[1] = normalize(dimTwo, normMeanDimTwo,
    normMaxDimTwo);
}
return normalizedPosition;.
```

The color value for the pixel cell may then be calculated according to the HSI colors pace with the following values:

Hue=angle/360*6.0, wherein the "angle" is the angle in degrees between the vector and a starting vector 504.

Saturation=length*(1+1.0/3.0).

Intensity=1.2.

Figure 4C:
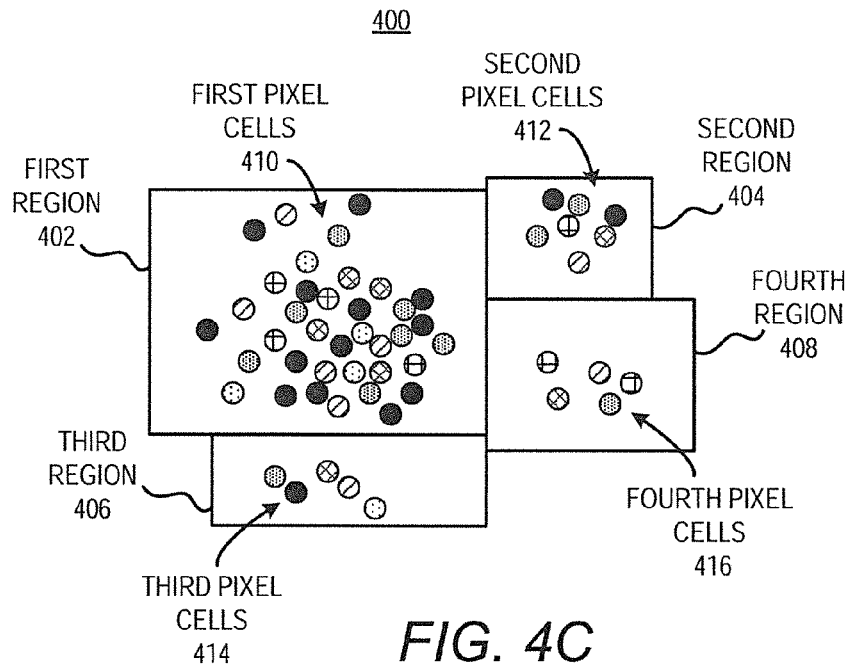

With reference back to FIG. 2, at block 212, the first pixel cells 410 and the second pixel cells 412 may be caused to be displayed on the distorted geographic map according to the determined respective color values. For instance, the processor 110 may implement the displaying/outputting module 132 to cause the first pixel cells 410 and the second pixel cells 412 to be displayed on the distorted geographic map 400 according to the determined respective color values. An example of the distorted geographic map 400 containing the pixel cells 410-416 is depicted in FIG. 4C. As shown in that figure, different ones of the pixel cells 410-416 may have different colors with respect to each other, in which the different colors denote that entities corresponding to the pixel cells 410-416 have different combinations of attributes with respect to each other.

According to an example, at block 212, the distorted geographic map displaying the first pixel cells 410 and the second pixel cells 412 may be caused to be displayed on a display through the input/output interface 112. In another example, at block 212, the distorted geographic map displaying the first pixel cells 410 and the second pixel cells 412 may be caused to be outputted to another device 116, e.g., another computing device, through the input/output interface 112. By way of particular example, the distorted geographic map may be outputted over the Internet from the computing device 102 to the output device 116.

Turning now to FIG. 3, at block 302, data pertaining to a plurality of entities may be accessed, in which the data includes the geographic locations of the plurality of entities and variables corresponding to the plurality of entities. For instance, the processor 110 may implement the data accessing module 120 to access the data. In addition, the processor 110 may implement the data accessing module 120 to access the data from any of a number of sources. For instance, the processor 110 may access the data pertaining to the entities from publicly and/or privately available data sources. In another example, the data may have been stored in the data store 114 and the processor 110 may access the data from the data store 114.

At block 304, blocks 202-212 of the method 200 may be implemented to cause the first pixel cells 410 and the second pixel cells 412 to be displayed on the distorted geographic map 400 according to the determined respective color values as discussed above with respect to block 212. Thus, following block 304, the distorted map 400 as depicted in FIG. 4C may be displayed to a user.

Figure 6A:
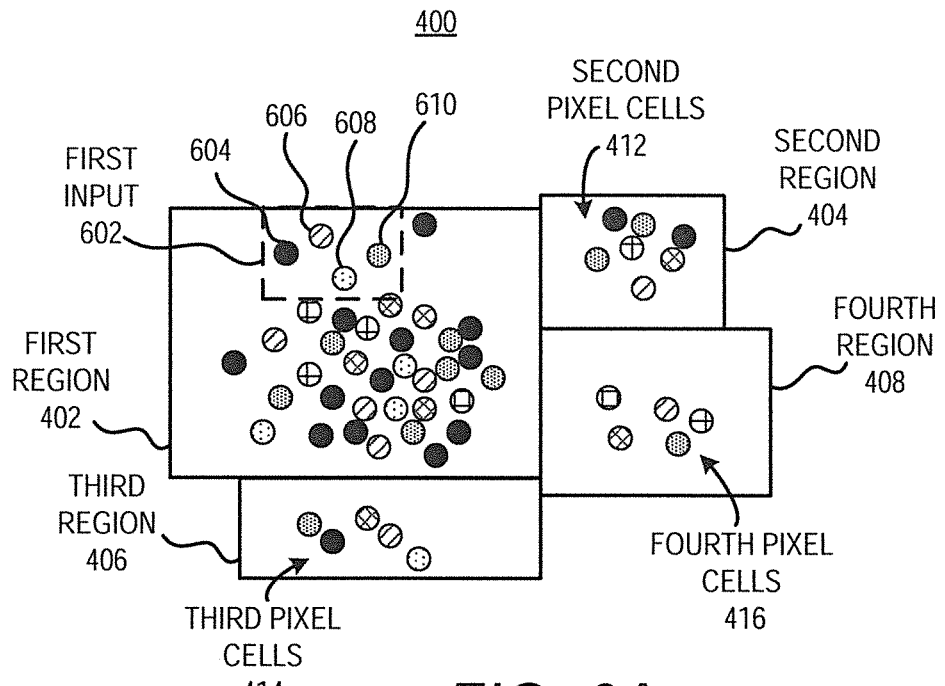
FIGS. 6A-6C, respectively, depict a geographic map, a two-dimensional graph, and a second geographic map, which may be generated at various stages of implementation of the method depicted in FIG. 3, according to an example.

At block 306, a first input may be received, in which the first input selects a subset of at least one of the first pixel cells 410 and the second pixel cells 412. For instance, the processor 110 may implement the input receiving module 134 to receive the first input from the user. According to an example, the first input may be a rubber-banded section of the geographic map 400. For instance, as shown in FIG. 6A, the first input 602 may be a rubber-banded section that include a plurality of pixel cells 604-610. The rubber-banded section may denote an area that is highlighted by a user.

Figure 6B:
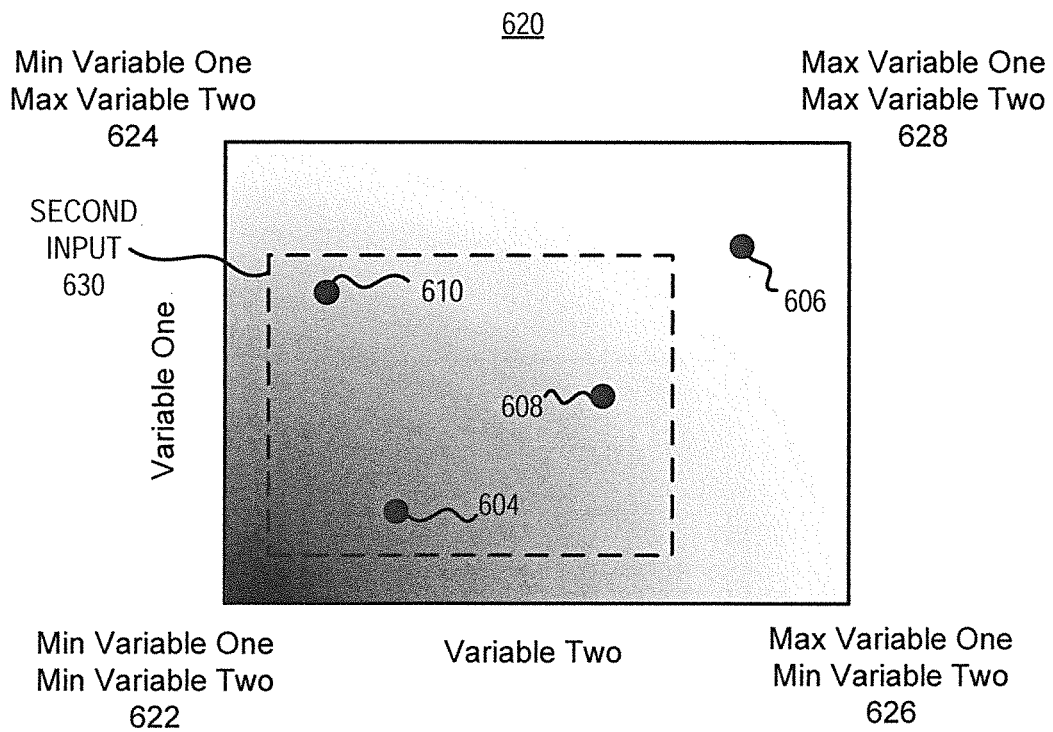

At block 308, in response to receipt of the first input 602, a two-dimensional graph that depicts an arrangement of the selected subset of the at least one of the first pixel cells and the second pixel cells according to the two variables corresponding to the plurality of entities may be generated. For instance, the processor 110 may implement the generating module 122 to generate the two-dimensional graph. An example of the two-dimensional graph 620 is depicted in FIG. 6B. As shown in FIG. 6B, the two-dimensional graph 620 includes a y-axis that represents a first variable (variable one) and an x-axis that represents a second variable (variable two). The graph 620 is also depicted as including four corners, in which each of the corners represents a pair of values of the first variable and the second variable. A first corner 622 represents a minimum value of the first variable and a minimum value of the second variable. A second corner 624 represents a minimum value of the first variable and a maximum value of the second variable. A third corner 626 represents a maximum value of the first variable and a minimum value of the second variable. A fourth corner 628 represents a maximum value of the first variable and the maximum value of the second variable.

As also shown in FIG. 6B, each of the pixel cells 604-610 in the subset identified in the first input 602 in FIG. 6A is depicted as being plotted within the graph 620. That is, the pixel cells 604-610 are depicted as being plotted in the graph 620 according to the first and second variables of the entities to which the pixel cells 604-610 respectively correspond. Thus, for instance, a pixel cell 604 may correspond to an entity having a lower first variable and a lower second variable than the entity to which a pixel cell 606 corresponds.

At block 310, the two-dimensional graph 620 including the pixel cells 604-610 may be displayed. For instance, the processor 110 may implement the displaying/outputting module 132 to display the two-dimensional graph 620 on the input/output device 116. The graphical depiction of the pixel cells 604-610 in the graph 620 may therefore enable a user to relatively easily see the differences between the entities represented by the pixel cells 604-610.

At block 312, a second input may be received, in which the second input selects a further subset of the first pixel cells depicted in the two-dimensional graph. For instance, the processor 110 may implement the input receiving module 134 to receive the second input from a user. According to an example, the second input may be a rubber-banded section of the two-dimensional graph. For instance, as shown in FIG. 6B, the second input 630 may be a rubber-banded section that includes a further subset of the pixel cells 604-610 selected in the first input 602.

At block 314, in response to receipt of the second input 630, a second geographic map that depicts the further subset of the first pixel cells may be generated according to the respective geographic locations of the plurality of entities corresponding to the further subset of the first pixel cells. For instance, the processor 110 may implement the generating module 122 to generate the second geographic map. An example of the second geographic map 650 is depicted in FIG. 6C.

Figure 6C:
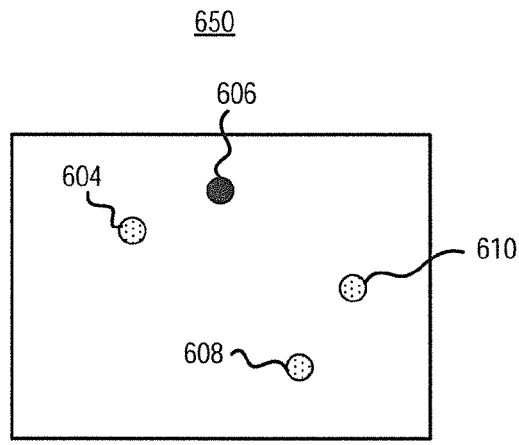

As shown in FIG. 6C, the second geographic map 650 may be an enlarged section of the geographic map 400 depicted in FIG. 6A. Particularly, the second geographic map 650 may be an enlarged portion of the section selected as the first input 602. In other examples, however, the second geographic map 650 may depict other portions of the geographic map 400.

As also shown in FIG. 6C, the pixel cells 604, 608, and 610 that were included in the second input 630 (FIG. 6B) may be highlighted such that these pixel cells are differentiated from the pixel cell 606, which was not included in the second input 630. In the second geographic map 650, the pixel cells 604, 608 and 610 may have a different color or may have some other feature to distinguish those pixel cells from the pixel cell 606. In one regard, therefore, the second geographic map 650 may graphically show the locations of the entities identified by the user as having the values of the desired pairs of first and second variables. In another example, only those pixel cells 604, 608, and 610 that were included in the second input 630 may be depicted in the second geographic map 650.

At block 316, the second geographic map 650 including the highlighted pixel cells 604, 608, and 610 may be displayed. For instance, the processor 110 may implement the displaying/outputting module 132 to display the second geographic map 650 on the input/output device 116. A user may select one the entities corresponding to the pixel cells 604, 608, and 610 as a final desired entity. In one regard, therefore, the method 300 may enable a user to interact with the display of the pixel cells 410, 412 and the geographic map 400.

According to a particular example, the entities are hospitals, a first variable is hospital charges, and a second variable is services quality (e.g., re-admit ratio). In this example, data pertaining to the hospitals may be accessed from publically available information, such as information available from the Center for Medicare and Medicaid Services. In addition, the geographic locations of the hospitals may be plotted on a geographic map as first pixel cells and second pixel cells (block 202). An example of a geographic map on which pixel cells have been plotted on multiple regions is depicted in the diagram 700 in FIG. 7A. As shown in that diagram 700, the geographic map is of the United States, and each of the regions is a particular state. In addition, it may also be seen that the hospitals in some of the more populated areas, such as Los Angeles and New York City, are in a relatively more dense formation as compared with other areas and thus, there is a relatively high level of overlap among those pixel cells. Moreover, although not explicitly depicted due to the limitations of the black-and-white image, each of the pixel cells representing a hospital may be displayed with a color that denotes, for instance, an average hospital charge.

Figure 7A:
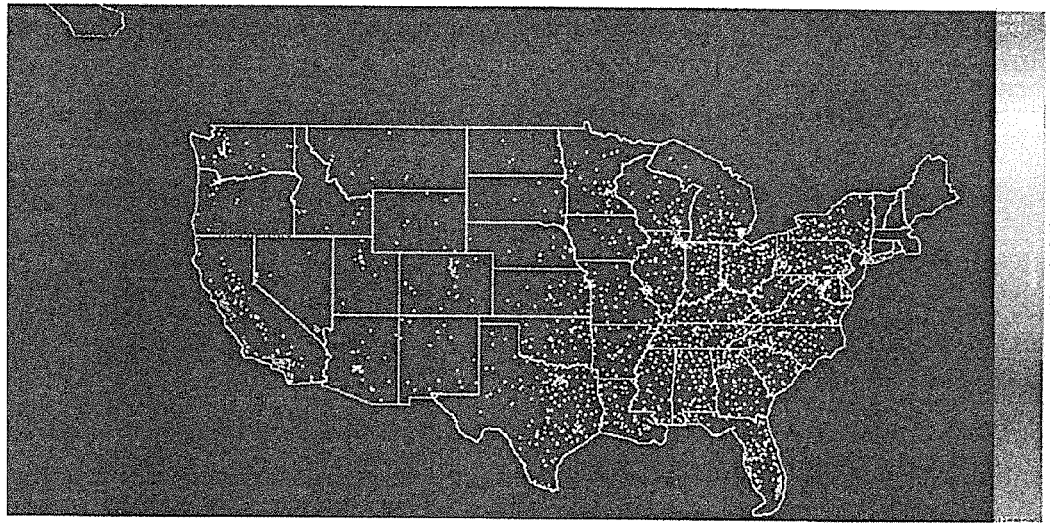
FIGS. 7A-7E, respectively, depict diagrams pertaining to a particular set of entities in which the methods disclosed herein are implemented, according to an example.
Figure 7B:
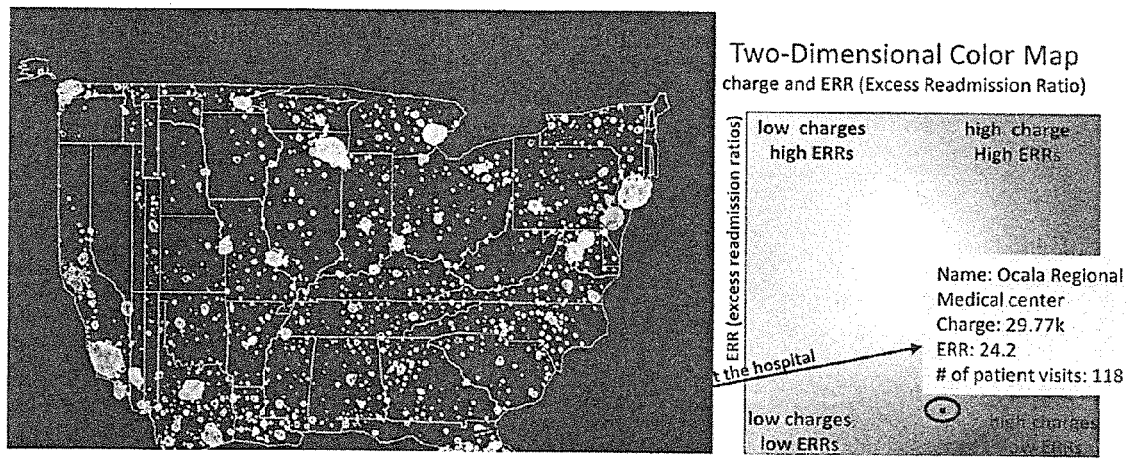

Turning now to FIG. 7B, there is shown a diagram 710, which depicts a distorted version of the geographic map depicted in the diagram 700, and which may have been generated and displayed through implementation of blocks 202-212 (FIG. 2). As may be seen in the diagram 710, the regions containing Los Angeles and New York City have been enlarged to thus enable the pixel cells representing the hospitals in those locations to either not overlap each other or to substantially minimize the amount of overlap among those pixel cells. As also shown, other regions containing a relatively sparser arrangement of pixel cells are reduced in sized. Moreover, although not explicitly depicted due to the limitations of the black-and-white image, each of the pixel cells representing a hospital may be displayed with a color according to the two-dimensional color map shown in the diagram 710. The colors in the color map denote two variables, hospital charges and excess readmission ratios, and may be generated as discussed above.

Figures 7C, 7D, 7E:
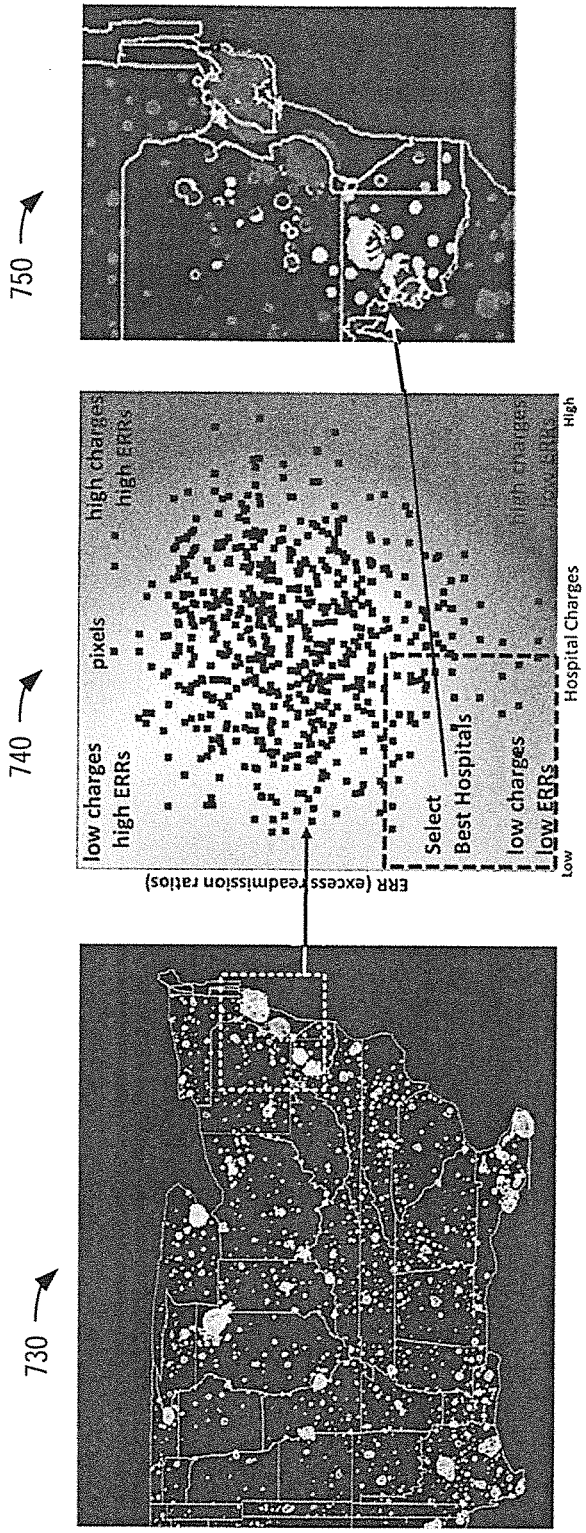

With reference now to FIG. 7C, there is shown a diagram 730, which is similar to the diagram 7B, but depicts a first input that selects a subset of a first set of pixel cells as denoted by the dashed box (FIG. 3, block 306). In this example, the first input is of an area of the East Coast. Responsive to receipt of the first input, a two-dimensional graph may be generated and displayed, as shown in the diagram 740 in FIG. 7D, and as discussed in greater detail with respect to blocks 308 and 310 (FIG. 3). As shown, the two-dimensional graph depicts pixel cells of the hospitals in the area selected from the geographic map (FIG. 7O) according to the amounts that the respective hospitals charge and their excess readmission ratios. Thus, the hospitals in the bottom left section of the graph may be identified as having the lowest charges and the lowest excess readmission ratios.

A second input that selects a subset of the pixel cells depicted in the two-dimensional graph may be received (FIG. 2, block 312). The second input selection is denoted by the dashed box in FIG. 7D. In this example, the second input is of the hospitals located in the bottom left section of the graph. Responsive to receipt of the second input, a second geographic map that depicts the subset of the pixel cells depicted in the graph is generated and displayed, as shown in the diagram 750 in FIG. 7E, and as also discussed in greater detail with respect to blocks 314 and 316 (FIG. 3). As shown, the second geographic map is an enlarged portion of the geographic map depicted in the diagram 710 in which the selected subset of pixel cells are depicted. That is, for instance, the second geographic map may depict only those pixel cells that are included in the dashed box of the second input. In other examples, additional pixel cells may be depicted in the second geographic map, but the selected pixel cells may be distinguished from those additional pixel cells through, for instance, different colors, flashing, embellishments, etc. In any regard, the pixel cells depicted in the diagram 750 may be displayed to have colors that correspond to the colors indicated in the two-dimensional graph depicted in FIG. 7D.

In the examples depicted in FIGS. 7A-7E, the user may be a health insurance payee or an insurance company who is interested in evaluating geographic variations in payments and quality of services. For example, a hospital that wants to improve outreach of cancer screening services to the community may implement the methods 200 or 300 to quickly identify local neighborhoods that have reduced access to care. Similarly, an insurance company may implement the methods 200 or 300 to identify high users of health care services, and develop preventive medicine policies that reduce cost and improve the quality of care. Visualizing spatial patterns of services as provided through implementation of the methods 200 or 300 may allow the end user to determine the effect of specific policies or to detect anomalous patterns such as disease outbreaks.

Although a particular example directed to hospitals has been described, it should be understood that the methods and apparatuses disclosed herein may be applied to other applications, such as revenue, energy, oil/gas industries, etc. Other examples in which the methods and apparatuses disclosed herein may be applied include, for instance, large scale agricultural businesses to use geospatial data to track plant disease and predict the spread of the plant disease based on weather patterns, nationwide call centers to discover patterns in customer satisfaction that lead to an early detection of product issues, etc.

Some or all of the operations set forth in the methods 200 and 300 may be contained as utilities, programs, or subprograms, in any desired computer accessible medium. In addition, the methods 200 and 300 may be embodied by computer programs, which may exist in a variety of forms both active and inactive. For example, they may exist as machine readable instructions, including source code, object code, executable code or other formats. Any of the above may be embodied on a non-transitory computer readable storage medium.

Examples of non-transitory computer readable storage media include conventional computer system RAM, ROM, EPROM, EEPROM, and magnetic or optical disks or tapes. It is therefore to be understood that any electronic device capable of executing the above-described functions may perform those functions enumerated above.

Figure 8:
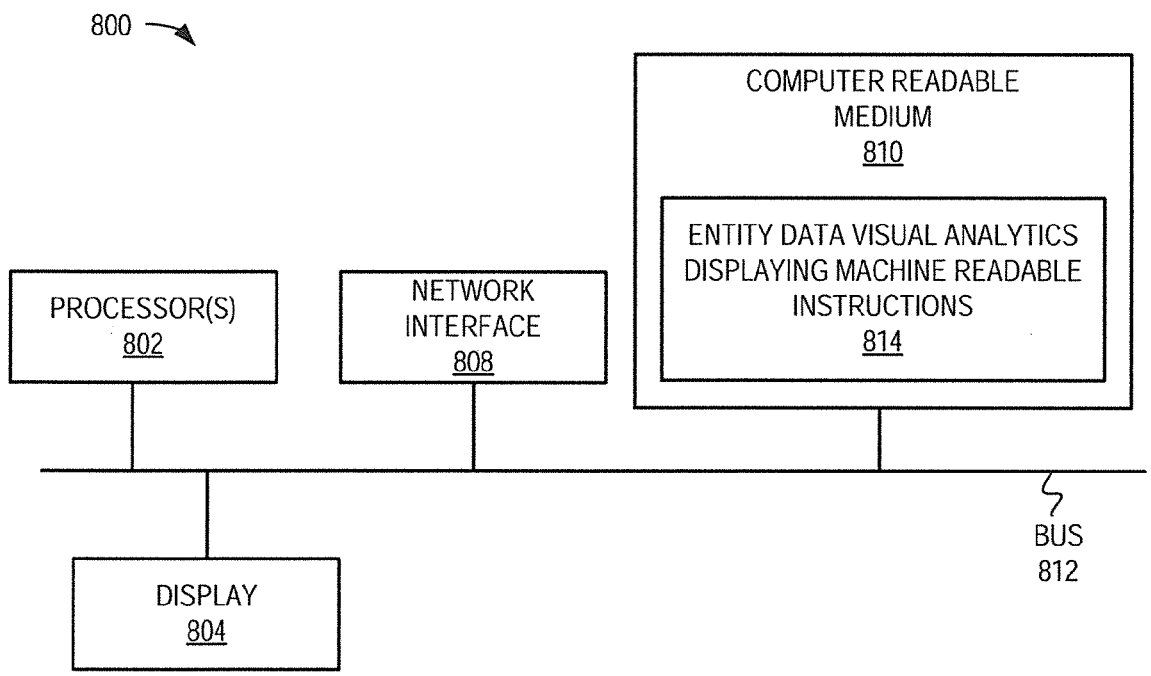
FIG. 8 is schematic representation of a computing device, which may be employed to perform various functions of the computing device depicted in FIG. 1, according to an example of the present disclosure.

Turning now to FIG. 8, there is shown a schematic representation of a computing device 800, which may be employed to perform various functions of the computing device 102 depicted in FIG. 1, according to an example. The computing device 800 may include a processor 802, a display 804, such as a monitor; a network interface 808, such as a Local Area Network LAN, a wireless 802.11x LAN, a 3G mobile WAN or a WiMax WAN; and a computer-readable medium 810. Each of these components may be operatively coupled to a bus 812. For example, the bus 812 may be an EISA, a PCI, a USB, a FireWire, a NuBus, or a PDS.

The computer readable medium 810 may be any suitable medium that participates in providing instructions to the processor 802 for execution. For example, the computer readable medium 810 may be non-volatile media, such as an optical or a magnetic disk; volatile media, such as memory. The computer-readable medium 810 may also store an entity data visual analytics displaying machine readable instructions 814, which may perform the methods 200 and/or 300 and may include the modules 120-134 of the entity data visual analytics displaying apparatus 104 depicted in FIG. 1. In this regard, the entity data visual analytics displaying machine readable instructions 814 may include a data accessing module 120, a generating module 122, a pixel cell overlap determining module 124, a geographic map distorting module 126, a pixel cell arranging module 128, a color value determining module 130, a displaying/output module 132, and an input receiving module 134.

Although described specifically throughout the entirety of the instant disclosure, representative examples of the present disclosure have utility over a wide range of applications, and the above discussion is not intended and should not be construed to be limiting, but is offered as an illustrative discussion of aspects of the disclosure.

What has been described and illustrated herein is an example of the disclosure along with some of its variations. The terms, descriptions and figures used herein are set forth by way of illustration only and are not meant as limitations. Many variations are possible within the spirit and scope of the disclosure, which is intended to be defined by the following claims—and their equivalents—in which all terms are meant in their broadest reasonable sense unless otherwise indicated.

What is claimed is:

1. A method for displaying visual analytics of entity data, said method comprising:
    plotting geographic locations of a plurality of entities as first pixel cells on a first region and as second pixel cells on a second region of a geographic map;
    determining that the first pixel cells have a higher degree of overlap with each other in the first region compared to the second pixel cells in the second region;
    distorting the geographic map to enlarge the first region;
    arranging the first pixel cells in the first region in a manner that prevents the first pixel cells from overlapping each other;
    determining a color value for each of the first pixel cells and the second pixel cells from a multi-paired color map that represents two variables corresponding to the plurality of entities by color; and
    cause, by a processor, the first pixel cells and the second pixel cells to be displayed on the distorted geographic map according to the determined respective color values.

2. The method according to claim 1, further comprising:
    accessing data pertaining to the plurality of entities, wherein the data includes the geographic locations of the plurality of entities and the two variables corresponding to the plurality of entities.

3. The method according to claim 1, further comprising:
    receiving a first input that selects a subset of at least one of the first pixel cells and the second pixel cells; and
    in response to receipt of the first input, generating a two-dimensional graph that depicts an arrangement of the selected subset of the at least one of the first pixel cells and the second pixel cells according to the two variables corresponding to the plurality of entities.

4. The method according to claim 3, further comprising:
    receiving a second input that selects a further subset of the first pixel cells depicted in the two-dimensional graph; and
    in response to receipt of the second input, generating a second geographic map that depicts the further subset of the first pixel cells according to the respective geographic locations of the plurality of entities corresponding to the further subset of the first pixel cells.

5. The method according to claim 4, wherein generating the second geographic map further comprises generating the second geographic map to be an enlarged portion of the geographic map in which the selected further subset of the first pixel cells are depicted.

6. The method according to claim 4, wherein the first input comprises a rubber-banded section of the geographic map and the second input comprises a rubber-banded section of the two-dimensional graph.

7. The method according to claim 1, wherein distorting the geographic map further comprises:
    determining a density of the first pixel cells in the first region;
    determining a density of the second pixel cells in the second region; and
    distorting the geographic map to distort the first region and the second region based upon the relative densities of the first pixel cells in the first region and the second pixel cells in the second region.

8. The method according to claim 1, wherein arranging the first pixel cells in the first region in a manner that prevents the first pixel cells from overlapping each other further comprises:
    positioning an initial pixel cell at a first location in the first region;
    determining that a next pixel cell is to overlap the initial pixel cell;
    iterating through data points around the first location in an ordered manner to identify an empty location; and
    positioning the next pixel cell at the empty location.

9. The method according to claim 1, wherein the plurality of entities comprise a plurality of hospitals.

10. An apparatus for displaying visual analytics of entity data, said apparatus comprising:

a processor;

a memory on which is stored machine readable instructions to cause the processor to:

access data pertaining to a plurality of entities, wherein the data includes the geographic locations of the plurality of entities and two variables corresponding to the plurality of entities;

plot geographic locations of the plurality of entities as first pixel cells on a first region and as second pixel cells on a second region of a geographic map;

determine that the first pixel cells have a higher degree of overlap with each other in the first region compared to the second pixel cells in the second region;

distort the geographic map to enlarge the first region;

arrange the first pixel cells in the first region in a manner that prevents the first pixel cells from overlapping each other;

determine a color value for each of the first pixel cells and the second pixel cells from a multi-paired color map that represents the two variables corresponding to the plurality of entities by color; and cause the first pixel cells and the second pixel cells to be displayed on the distorted map, wherein the first pixel cells and the second pixel cells have colors corresponding to the determined respective color values.

11. The apparatus according to claim 10, wherein the machine readable instructions are further to cause the processor to:

receive a first input that selects a subset of at least one of the first pixel cells and the second pixel cells; and in response to receipt of the first input, generate a two-dimensional graph that depicts an arrangement of the selected subset of the at least one of the first pixel cells and the second pixel cells according to the two variables corresponding to the plurality of entities.

12. The apparatus according to claim 10, wherein the machine readable instructions are further to cause the processor to:

receive a second input that selects a further subset of the first pixel cells depicted in the two-dimensional graph; and in response to receipt of the second input, generate a second geographic map that depicts the further subset of the first pixel cells according to the respective geographic locations of the plurality of entities corresponding to the further subset of the first pixel cells.

13. The apparatus according to claim 11, wherein, to distort the geographic map, the machine readable instructions are further to cause the processor to determine a density of the first pixel cells in the first region;

determine a density of the second pixel cells in the second region; and distort the geographic map to distort the first region and the second region based upon the relative densities of the first pixel cells in the first region and the second pixel cells in the second region.

14. The apparatus according to claim 11, wherein, to arrange the first pixel cells in the first region in a manner that prevents the first pixel cells from overlapping each other, the machine readable instructions are further to cause the processor to:

position an initial pixel cell at a first location in the first region;

determine that a next pixel cell is to overlap the initial pixel cell;

iterate through data points around the first location in an ordered manner to identify an empty location; and position the next pixel cell at the empty location.

15. A non-transitory computer readable storage medium on which is stored machine readable instructions that when executed by a processor cause the processor to:

plot geographic locations of a plurality of entities as first pixel cells on a first region and as second pixel cells on a second region of a geographic map;

determine that the first pixel cells have a higher degree of overlap with each other in the first region compared to the second pixel cells in the second region;

distort the geographic map to enlarge the first region;

arrange the first pixel cells in the first region in a manner that prevents the first pixel cells from overlapping each other;

determine a color value for each of the first pixel cells and the second pixel cells from a multi-paired color map that represents two variables corresponding to the plurality of entities by color; and cause the first pixel cells and the second pixel cells to be displayed on the distorted map, wherein the first pixel cells and the second pixel cells have colors corresponding to the determined respective color values.

* * * * *